US012648725B2

(12) United States Patent
Heidari et al.

(10) Patent No.: US 12,648,725 B2
(45) Date of Patent: Jun. 9, 2026

(54) BIOMAGNETISM MEASUREMENT SYSTEM FOR SENSING BIOMAGNETIC SIGNALS

(71) Applicants: THE UNIVERSITY COURT OF THE UNIVERSITY OF GLASGOW, Glasgow (GB); THE UNIVERSITY COURT OF THE UNIVERSITY OF EDINBURGH, Edinburgh (GB)

(72) Inventors: Hadi Heidari, Glasgow (GB); Siming Zuo, Glasgow (GB); Kianoush Nazarpour, Edinburgh (GB)

(73) Assignees: THE UNIVERSITY COURT OF THE UNIVERSITY OF GLASGOW, Glasgow (GB); THE UNIVERSITY COURT OF THE UNIVERSITY OF EDINBURGH, Edinburgh (GB)

( * ) Notice: Subject to any disclaimer, the term of this patent is extended or adjusted under 35 U.S.C. 154(b) by 0 days.

(21) Appl. No.: 19/114,017

(22) PCT Filed: Sep. 21, 2023

(86) PCT No.: PCT/EP2023/076144
§ 371 (c)(1),
(2) Date: Mar. 21, 2025

(87) PCT Pub. No.: WO2024/062068
PCT Pub. Date: Mar. 28, 2024

(65) Prior Publication Data
US 2026/0102094 A1      Apr. 16, 2026

(30) Foreign Application Priority Data

Sep. 22, 2022      (GB) ...................................... 2213839
Sep. 20, 2023      (GB) ...................................... 2314428

(51) Int. Cl.
A61B 5/242      (2021.01)
A61B 5/00       (2006.01)
A61B 5/307      (2021.01)

(52) U.S. Cl.
CPC .............. *A61B 5/242* (2021.01); *A61B 5/307* (2021.01); *A61B 5/6831* (2013.01);
(Continued)

(58) Field of Classification Search
CPC ........................ A61B 5/242; A61B 2562/0223
See application file for complete search history.

(56) References Cited

U.S. PATENT DOCUMENTS 5,122,744 A      6/1992  Koch
5,187,436 A      2/1993  Mallick
(Continued)

OTHER PUBLICATIONS

International Search Report and Written Opinion issued in PCT/EP2023/076144 mailed Nov. 14, 2023.
(Continued)

*Primary Examiner* — Colin T. Sakamoto
(74) *Attorney, Agent, or Firm* — MEDLER FERRO WOODHOUSE & MILLS PLLC

(57)      ABSTRACT

A biomagnetic sensor that incorporates an integrated active noise cancellation unit that uses a gradiometer to remove ambient magnetic noise from a detection signal obtained from a tunnelling magnetoresistive (TMR) sensor unit that is indicative of a magnetic field adjacent to biological tissue. The ambient magnetic noise can thus be removed in real time at a front end of the sensor (e.g. as part of circuitry in the sensor body itself). The active noise cancellation technique proposed herein may be effective enough to enable the biomagnetic sensor to be used in an unshielded environment
(Continued)

(i.e. an environment that is subject to the Earth's magnetic field, for example), which widens significantly the potential uses for the sensor.

20 Claims, 12 Drawing Sheets

(52) U.S. Cl.
CPC .......... *A61B 5/7203* (2013.01); *A61B 5/4519* (2013.01); *A61B 2560/0247* (2013.01); *A61B 2560/0462* (2013.01); *A61B 2562/0223* (2013.01); *A61B 2562/046* (2013.01); *A61B 2562/18* (2013.01)

(56) References Cited

U.S. PATENT DOCUMENTS

| | | | | |
|---|---|---|---|---|
| 6,208,884 B1 * | 3/2001 | Kumar | .................. | A61B 5/055 |
| | | | | 324/207.21 |
| 6,418,335 B2 * | 7/2002 | Avrin | ................... | A61B 5/416 |
| | | | | 324/207.21 |
| 6,496,713 B2 * | 12/2002 | Avrin | ................... | A61B 5/242 |
| | | | | 324/207.21 |
| 6,965,792 B2 * | 11/2005 | Avrin | ................... | A61B 5/242 |
| | | | | 600/407 |
| 7,047,059 B2 * | 5/2006 | Avrin | .................... | A61B 5/242 |
| | | | | 324/207.21 |
| 10,247,789 B2 | 4/2019 | Kandori et al. | | |
| 2001/0029329 A1 * | 10/2001 | Avrin | ....................... | A61B 5/05 |
| | | | | 600/407 |
| 2002/0077537 A1 * | 6/2002 | Avrin | ....................... | G01V 3/08 |
| | | | | 600/408 |
| 2002/0151779 A1 * | 10/2002 | Avrin | ..................... | A61B 5/242 |
| | | | | 600/407 |
| 2014/0062472 A1 * | 3/2014 | Nishikawa | ............. | A61B 5/245 |
| | | | | 324/252 |
| 2023/0012505 A1 | 1/2023 | Heidari et al. | | |

OTHER PUBLICATIONS

Great Britain Search Report issued in FB 2213839.0 dated Mar. 5, 2023.
Great Britain Search Report issued in GB 2314428.0 dated Jan. 31, 2024.
Zhao et al., "Tunnel Magnetoresistance Sensor with AC Modulation and Impedance Compensation for Ultra-Weak Magnetic Field Measurement", Sensors, Jan. 28, 2022, vol. 22, No. 1021, pp. 1-13.
Luong Van-Su et al., "Reduction of Low-Frequency Noise in Tunneling-Magnetoresistance Sensors With a Modulated Magnetic Shielding", IEEE Transactions on Magnetics, IEEE, USA, Nov. 1, 2014, vol. 50, No. 11, pp. 1-4.

* cited by examiner

| 116 | Power management | Wireless communication | 114 |
| 109 | Control circuitry | | 112 |
| | Analogue read out circuitry | | 110 |
| | Active noise cancellation | | 111 |
| 103 | Secondary sensing layer | | 108 |
| | Shielding layer | | 106 |
| | Primary sensing layer | | 104 |
| | Skin interface | | 102 |

100

206    204

206    218

20 mm

208

Single MTJ Element

212 — Free layer
214 — Tunnel barrier
216 — Reference layer

210

D 4 mm 6 mm

BIOMAGNETISM MEASUREMENT SYSTEM FOR SENSING BIOMAGNETIC SIGNALS

CROSS-REFERENCE TO PRIOR APPLICATIONS

This application is a § 371 National Stage Application of PCT International Application No. PCT/EP2023/076144 filed Sep. 21, 2023, which claims priority to UK Patent Application No. GB 2314428.0 filed Sep. 20, 2023, and UK Patent Application No. GB 2213839.0 filed Sep. 22, 2022, each of which are incorporated herein in their entirety.

FIELD OF THE INVENTION

The present invention relates to a system for measuring biomagnetism and particularly, although not exclusively, to a wearable device for sensing biomagnetic signals. The system may incorporate magnetic field sensor chip that utilises a tunnelling magnetoresistive (TMR) array in conjunction active on-chip noise cancellation.

BACKGROUND

It is known that muscle activity can be recorded with electrical sensors by surface (on-skin) or depth (in-muscle tissue) electromyography (EMG). A significant challenge with EMG is the lower spatial resolution of the sensors, which make it difficult to record selectively from single motor units within a muscle. The spatial resolution can be enhanced using intramuscular EMG in which needle electrodes are pushed into the muscle tissue, but this is painful and damages muscle functions. Moreover, in chronic implants, such as for the motor rehabilitation, the interface between the metal contacts of the sensor and the human tissue changes overtime, leading to infection and rejection by the body.

With the rapid progress of micro- and nano-technology, non-invasive assessment of biomagnetism has emerged as an alternative paradigm to EMG. Biomagnetic signals have the same temporal resolution as the corresponding bioelectric signals but can offer significantly higher spatial resolution. Sensing magnetic fields also does not require electric contacts during the recording and therefore the sensor can be fully encapsulated within biocompatible materials so as to minimise the risk of infection [6].

However, there remain technical challenges in providing a practical device capable of detecting biomagnetic signals, primarily due to the fact that biomagnetic signals have a very small amplitude. While a high temporal resolution may be achieved, the achievable spatial resolution is constrained due to a limit on sensor numbers, movement artifacts, intrinsically low signal-to-noise ratio (SNR), and relatively high static and dynamic background magnetic noise [9].

Initial attempts at developing sensor for detecting tiny biomagnetic fields explored the use of superconducting quantum interference devices (SQUIDs) [10] and optically-pumped magnetometers (OPMs) [5]. Both approaches were limited because they required the use of a large magnetically shielded room. These methods were bulky, costly, consumed large power and also needed a temperature-controlled environment.

More recently, spintronic sensors based on a magnetoresistive (MR) effect have revolutionised the approach to biomagnetic sensing owing to their full compatibility with traditional silicon technology. These sensors can be integrated with the readout circuitry onto a standard CMOS process in sub-mm diameter substrates to eventually realize the on-chip signal conditioning, including amplification, filtering, noise, and drift cancellation [11]. This phenomenon has led to the development of the MR sensors with ultra-high sensitivity, which have gradually replaced the traditional thin-film magneto-transport devices such as Hall sensors [12] and have the potential to detect pico-Tesla range magnetic fields, appropriate for biomagnetic signal level.

In addition, the miniaturized MR sensor area can improve the resolution of fields with small distance changes. The sensor placed at a closer distance to the neural sources will provide stronger signals. The MR sensors, thereby, are suitable for array applications with a lower power requirement. Recently, giant magnetoresistive (GMR) sensors were used to record weak biomagnetic signals. However, the sensitivity of GMR sensors is in the nano-Tesla range and therefore averaging was required to enhance the SNR. Over the last decade, sensing at pico-Tesla/√Hz level fields has become possible with the tunnelling magnetoresistive (TMR) sensors that are highly miniaturized and can be operated at room temperature using a sensor array.

Various potential applications for a biomagnetic sensor have been identified, from clinical diagnoses to human-computer-interaction [1]. However, the detection of weak biomagnetic fields derived from human active organs and tissues, including for example Magnetocardiography (MCG) [2], [3], Magnetoencephalography (MEG) [4], [5], Magnetomyography (MMG) [6], [7], Magnetoneurography (MNG) [8], requires effective methods that offer both high spatial and temporal resolutions.

SUMMARY OF THE INVENTION

At its most general, the present invention provides a biomagnetic sensor that incorporates an integrated active noise cancellation unit that uses a gradiometer to remove ambient magnetic noise from a detection signal obtained from a tunnelling magnetoresistive (TMR) sensor unit that is indicative of a magnetic field adjacent to biological tissue. The ambient magnetic noise can thus be removed in real time at a front end of the sensor (e.g. as part of circuitry in the sensor body itself). The active noise cancellation technique proposed herein may be effective enough to enable the biomagnetic sensor to be used in an unshielded environment (i.e. an environment that is subject to the Earth's magnetic field, for example), which widens significantly the potential uses for the sensor.

In a first aspect, the present invention may provide a biomagnetic sensor module comprising: a tunnelling magnetoresistive, TMR, sensor unit configured to output a detection signal indicative of a magnetic field adjacent to biological tissue; a gradiometer unit configured to output a background signal indicative of ambient magnetic noise; a shielding element located between the TMR sensor unit and the gradiometer unit; an active noise cancellation unit configured to remove the background signal from the detection signal to generate a biomagnetic signal; analogue read out circuitry configured to receive the biomagnetic signal and perform signal conditioning to generate an analogue output; and an analog-to-digital converter, ADC, arranged to generate a digital output signal from the analogue output.

Herein the term "biomagnetic" is used to refer to magnetic fields that are generated through electric activity in biological tissue, e.g. neural or muscle tissue. Typically such magnetic fields are very weak, so it is to be understood that a biomagnetic sensor is a device that is capable of detecting such weak fields, for example by having a sensitivity in the pico-Tesla range, e.g. a sensitivity equal to or less than 50 pT/NHz, preferably equal to or less than 20 pT/NHz.

The TMR sensor unit may comprise a plurality of TMR sensors, each of which has an array of magnetic tunnelling junctions fabricated on a substrate. The magnetic tunnelling junctions can be fabricated using known nanoscale techniques so that the array has a small footprint, e.g. equal to or less than 12 mm$^2$.

The plurality of TMR sensors in the TMR sensor unit may comprise four TMR sensors in a Wheatstone bridge arrangement.

The gradiometer unit may comprise a triaxial gradiometer. An advantage of this arrangement is that the background signal may provide a consistency indication of ambient magnetic noise irrespective of the orientation of the sensor module.

The gradiometer unit may use the same sensing modality as the TMR sensor unit. That is, the gradiometer unit may comprise a plurality of TMR sensors configured to detect ambient magnetic noise. The plurality of TMR sensors may be configured in the same manner as TMR sensors in the TMR sensor unit. For example, the gradiometer unit may comprise four TMR sensors in a Wheatstone bridge arrangement. Providing the same sensor configuration in both the gradiometer unit and the TMR sensor unit may make the background signal is directly comparable to the detection signal.

The biomagnetic sensor module may comprise a plurality of TMR sensor units, wherein each TMR sensor unit is arranged to detect a magnetic field adjacent to biological tissue and output a biomagnetic signal on a respective channel, and wherein the biomagnetic sensor module further comprise a multiplexer configured to selectively couple each respective channel to the analogue read out circuitry.

The biomagnetic sensor module may include a controller (e.g. microprocessor unit or the like) configured to control operation of the module.

The active noise cancellation unit may comprise a comparator (e.g. differential amplifier or equivalent) configured to receive the background signal and the detection signal as inputs, whereby the background signal is subtracted from the detection signal to generate a biomagnetic signal. The active noise cancellation unit may thus act directly on the outputs from the TMR sensor unit and the gradiometer unit, which facilitates real-time cancellation before further signal processing takes place.

The biomagnetic sensor module may be configured to bring the TMR sensor unit into proximity with a measurement location on a human or animal body. For example, the biomagnetic sensor module may comprise a skin contact interface made from biocompatible material. The skin contact interface may form an exterior surface, e.g. a base, of the biomagnetic sensor module. The TMR sensor unit may be disposed on the skin contact interface so that it lies as close as possible to the exterior surface. The skin contact interface may comprise a thermally insulating layer disposed between the TMR sensor unit and the exterior surface. The thermally insulating layer may inhibit thermal conduction so as to maintain the internal components of the biomagnetic sensor module (and in particular the TMR sensor unit and gradiometer unit) at a stable temperature.

The gradiometer unit may be located further from the skin contact interface than the TMR sensor unit.

This configuration can avoid background signal from the gradiometer unit being influenced by a magnetic field generated in the biological tissue. In one example, the gradiometer unit may be spaced more than 5 mm, preferably more than 10 mm, further from the exterior surface than the TMR sensor unit.

The shielding element located between the TMR sensor unit and the gradiometer unit acts to further reduce any effect of a magnetic field generated in the biological tissue on the background signal. The shielding element may be a magnetically permeable material, such as a nickel-molybdenum alloy. The shielding element may be provided in the form of a foil or other sheet-like material, e.g. as a layer to separate the TMR sensor unit and gradiometer unit. The shielding element may enable the physical separation of the TMR sensor unit and gradiometer unit to be minimized, e.g. to be equal to or less than 10 mm, without affecting the accuracy or sensitivity of measurement.

The biomagnetic sensor module may further comprise a compensation unit configured to minimize a baseline mismatch between the TMR sensor unit and gradiometer unit, which can be caused by a combination of intrinsic mismatch between the sensors of the TMR sensor unit and gradiometer unit and the effect of the shielding element. Here the reference to "baseline" means measurements obtained in the absence of a target signal, i.e. when the TMR sensor unit is not disposed on skin. The compensation unit may comprise a feedback circuit configured to receive a baseline output from the TMR sensor and gradiometer unit and adjust the gradiometer unit to minimize the baseline output. In one example, the compensation unit may comprise an adjustable current source configured to generate a bias signal for the gradiometer unit, wherein the bias signal is adjustable to minimize the baseline output. In another example, the compensation unit may comprise a variable gain amplifier connected between the gradiometer unit and the active noise cancellation unit, wherein the gain of the variable gain amplifier is adjustable to minimize the baseline output.

In one example, the biomagnetic sensor module may have a layered structure comprises a plurality of functional layer lying one on the other, for example with a skin contact interface layer at a base thereof. The TMR sensor unit may be arranged in a primary sensing layer and the gradiometer unit is arranged in a secondary sensing layer that lies parallel to and spaced from the primary sensing layer. In this context, the shielding element mentioned above may be provided as a layer between the primary sensing layer and the secondary sensing layer. The active noise cancellation unit and analogue read out circuitry may be arranged in one or more layers that lies parallel to and spaced from the secondary sensing layer. Further components, e.g. a controller, the ADC, and a power management unit may be arranged in one or more further layers. All of the layers may be enclosed or otherwise held together by a housing or shell.

The analogue read out circuitry may be configured to eliminate input offset and low frequency flicker noise. For example, the analogue read circuitry may comprise a bandpass filter and a common mode feedback circuit.

The biomagnetic sensor module may further comprise a wireless communication unit configured to transmit the digital output signal to a remote device. The remote device may be a smartphone, tablet, laptop, or desktop device. The wireless communication unit may be configured to transmit the data using any suitable wireless protocol (e.g. Bluetooth® or the like). The wireless communication unit may also be capable of receiving information from the remote device, e.g. to control operation of the module or update its firmware.

In another aspect, the invention may provide a wearable biomagnetic sensing device comprising the biomagnetic sensor module set out above. The wearable biomagnetic sensing device may be operable in an unshielded environment. The wearable biomagnetic sensing device may form part of a measurement system that also includes a remote computing device in communication with the biomagnetic sensor module, e.g. to receive the digital output signal.

In one example, the wearable biomagnetic sensing device may comprise a plurality of the biomagnetic sensor modules discussed above secured to a retaining element that is mountable on a human body. The retaining element may be an elastic strap so that the device can be retained around a user's arm or leg.

The invention includes the combination of the aspects and preferred features described except where such a combination is clearly impermissible or expressly avoided.

SUMMARY OF THE FIGURES

Embodiments and experiments illustrating the principles of the invention will now be discussed with reference to the accompanying figures in which.

DETAILED DESCRIPTION OF THE INVENTION

Aspects and embodiments of the present invention will now be discussed with reference to the accompanying figures. Further aspects and embodiments will be apparent to those skilled in the art. All documents mentioned in this text are incorporated herein by reference.

The present invention relates to a biomagnetism measurement system, and in particular to a wearable biomagnetic sensing device and biomagnetic sensing module used in such a device. The aim of the biomagnetism measurement system is to detect or estimate the biomagnetic potential associated with muscle activity in a non-invasive manner at room temperature. Such a system may enable greater understanding of what happens to the muscle in the area that controls the movement of the limb.

As set out in more detail below, the biomagnetic sensing module provides on-chip and real-time noise cancellation functionality that reduces or eliminates noise from the environment (e.g. Earth's magnetic field, thermal and 1/f noise) by combining multiple device and circuits techniques. With these techniques, the biomagnetic sensing module discussed herein can, for the first time, achieve non-invasive recording of the magnetic biomedical signals from neurons, nerves, and muscles at room temperature without external shielding.

Generally speaking, a biomagnetism sensing device as discussed herein comprises one or more biomagnetic sensing modules that each comprise a plurality of sensors which in turn each have a plurality of tunnelling magnetoresistive (TMR) elements configured in an array, e.g. fabricated on a silicon substrate using conventional CMOS microfabrication techniques. Each sensing module may further include an integrated signal processing package, which comprises an analog readout circuit configured to generate an analog output that is delivered to an analog-to-digital converter (ADC). The ADC is connected to a microcontroller that includes a wireless communication module arranged to communicate a digital output signal to a remote device for analysis. The sensors in each module may be configured to output a signal on each of a plurality of channels. The analog readout circuit may be configured as a plurality of modular units (one for each channel) that are connectable to the ADC by a multiplexer. As discussed below, the integrated signal processing package provides noise cancelling functionality that can ensure that detected biomagnetic potentials are properly indicated in the output signals.

Figures 1, 2:
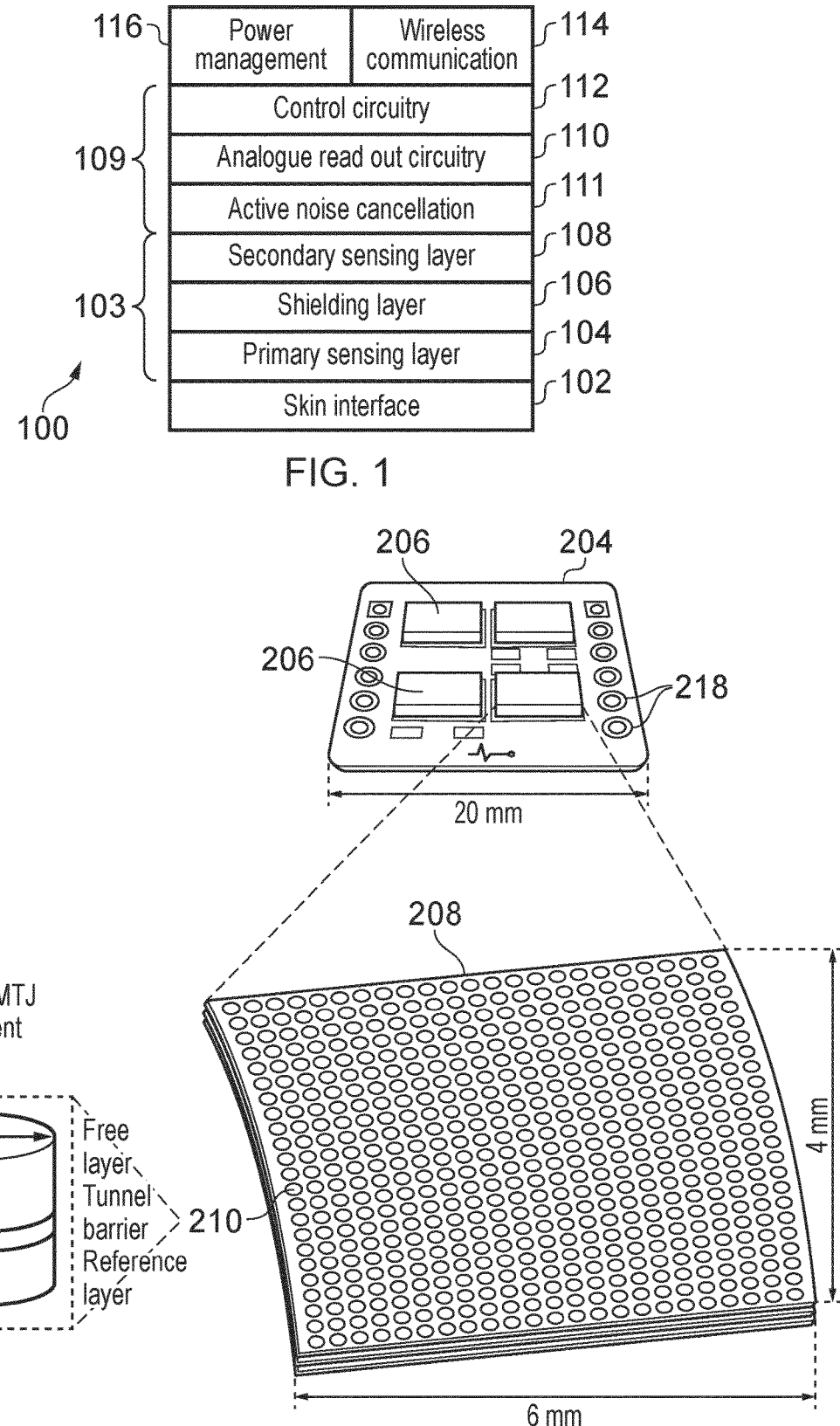
FIG. 1 is a schematic diagram illustrating a layered structure for a biomagnetic sensor module that is an embodiment of the invention.
FIG. 2 is a schematic diagram illustrating the constituent parts of a sensor array that can be used in the biomagnetic sensor module of FIG. 1.

FIG. 1 is a schematic diagram illustrating a layered structure for a biomagnetic sensor module 100 that is an embodiment of the invention. The biomagnetic sensor module 100 is configured for use with a wearable biomagnetic sensing device that is intended to be worn against a user's skin at a region where measurement is to take place.

The biomagnetic sensor module 100 in this example is configured in a layered structure, with each layer intended to lie parallel with a skin surface when worn. The layered structure comprises a skin interface 102 which may comprise a biocompatible material or coating on a bottom surface of the sensor module 100. Herein the terms "top"

and "bottom" in relation to the biomagnetic sensor module 100 may be understood to relate to intended orientation of the module relative to a skin surface when in use. That is, a bottom of the module is intended to lie closer to a skin surface than a top of the module when in use. The skin interface 102 may facilitate easy mounting and dismounting of the device in various positions without having to apply or remove gels and adhesives. Moreover, by using a biocompatible material, a comfortable fit can be ensured. Examples of suitable biocompatible materials include nanocellulose, biocompatible polymers, or e-skin.

The skin interface 102 may further comprise a thermally insulation layer, e.g. made from polyurethane or the like, arranged to insulate the components of the sensor module 100 from heat generated by the user's body when the device is worn. This can ensure that the sensor arrays within the device operate at a consistent temperature, and thereby avoid introducing errors caused by thermal variation.

Next to the skin interface 102 is a magnetic sensing substructure 103 that comprising three layers: a primary sensing layer 104, a shielding layer 106 and a secondary sensing layer 108. Each of the primary sensing layer 104 and the secondary sensing layer 108 comprises a plurality of tunnelling magnetoresistive (TMR) sensors, as discussed below. The shielding layer 106 operates to magnetically isolate the primary sensing layer 104 from the secondary sensing layer 108. The shielding layer 106 is preferably formed of a magnetically permeable material, such as a nickel-molybdenum alloy. In one example, the shielding layer 106 may be formed from MuMetal®, which has a composition of 80% nickel, 4.5% molybdenum and balance iron to provide high magnetic susceptibility. As is discussed below in more detail, the secondary sensing layer 108 is configured as a gradiometer to measure a background magnetic field potential that can be subtracted from the signal detected by the primary sensing layer 104 as part of the noise cancellation functionality provided by the sensor module 100. The shielding layer 106 operates to shield the biomagnetic field from the secondary sensing layer 108. The strength of the biomagnetic field naturally decreases with distance from the skin surface according to the inverse square law. As the secondary sensing layer 108 is already further from the skin interface 102 than the primary sensing layer 104, it will receive a weaker biomagnetic signal when in use. However, the shielding layer 106 strengthens that isolation and can ensure that a portion of the biomagnetic signal is not accidentally cancelled when the background magnetic field potential measured by the gradiometer is subtracted from the signal detected by the primary sensing layer 104.

FIG. 2 is a schematic diagram illustrating the constituent parts of a sensor unit 204 that can be used in the primary sensing layer 104 and secondary sensing layer 108. In this example, the sensor unit 204 is configured with four sensors 206 in a Wheatstone bridge structure to provide a signal on a first channel. The primary sensing layer 104 and secondary sensing layer 108 of the sensor module 100 may be configured with multiple channels (e.g. 8 or more), with the output of each channel being from an independent sensor unit 204 mounted in the relevant layer. Accordingly, each of the primary sensing layer 104 and secondary sensing layer 108 may comprises an assembly of sensor units 204.

Each of the sensors 206 in the sensor unit 204 comprises an array 208 of TMR sensor elements 210. Each TMR sensor element 210 in the array is a magnetic tunnelling junction comprising two layers of ferromagnetic material 212, 216 separated by a very thin insulation layer 214. The top layer 212 is defined as a free layer since its magnetization direction can be changed freely, and the bottom layer 216 is called a pinned layer due to its fixed magnetization orientation when the sensor is fabricated. The sensor is configured to permit a tunnelling effect in which electrons can pass through the insulating layer 214 under certain conditions, which in turn causes the structure to exhibit spin-related magnetoresistive properties at room temperature.

The response of a TMR sensor corresponds to a change in resistance across the device with variation in magnetic field. For biomagnetic measurement, it is desirable for the response to be linear and hysteresis-free. Typically, optimal noise performance is obtained with large arrays of large area sensors. In the example discussed herein, 1102 TMR sensor elements 210 are connected as 38 rows and 29 columns in series to minimize sensor 1/f noise. Each TMR sensor element 210 was formed from the following stack of layers (nm): 5 Ta/25 CuN/5 Ta/5 Ru/20 IrMn/2 CoFe$_{30}$/0.85 Ru/2.6 CoFe$_{40}$B$_{20}$/1 MgO [9 kΩ·μm2]/2 CoFe$_{40}$B$_{20}$/0.21 Ta/4 NiFe/0.20 Ru/6 IrMn/2 Ru/5 Ta/10 Ru. The size of each TMR element is 100×100 μm. The size of the array 208 is 6×4 mm, which means that the footprint of the sensor unit 204 can be controlled to be no more than 20 mm$^2$. Each array 210 on the sensor unit 204 is electrically connected to a respective electrode pad 218 through which it is connected to the remaining electronics.

A Wheatstone bridge structure is employed to minimize the temperature drift and also to nullify the output signal in the absence of any applied magnetic field. In the examples discussed herein, four sensors 206 of the type discussed above are arranged in a full Wheatstone bridge configuration. For a bias current of 20 mA, the measured linear range of the sensor is approximately –1 Oe to 1 Oe. With the full bridge setup, the measured resistance variation of each TMR sensor is 280 Ω·μm$^2$/Oe. Thus, for 1102 elements with the area of 100×100 μm$^2$, the sensitivity is calculated as ~0.617 V/Oe.

Returning to FIG. 1, the module 100 further comprises signal processing circuitry 109 arranged above the magnetic sensing substructure 103. The signal processing circuitry 109 is configured to perform on-device processing of signals received from the sensor units. The signal processing circuitry 109 comprises an active noise cancellation unit 111, analogue read out circuitry 110 and associated control circuitry 112, which may be arranged in respective layers, or which may be combined in one or more layers. The functionality of these layers is discussed in more detail below with reference to FIGS. 5 to 7.

The module 100 further comprises a wireless communication unit 114, which can be configured to communicate to communicate with a remote computer to send or receive data from the module. For example, the module 100 may be configured to transmit post-processed output signals from the sensor units to an external device for further analysis.

The module 100 further comprises a power management unit 116 which may include a battery (e.g. a Li-ion cell) and associated control circuitry.

Figure 3:
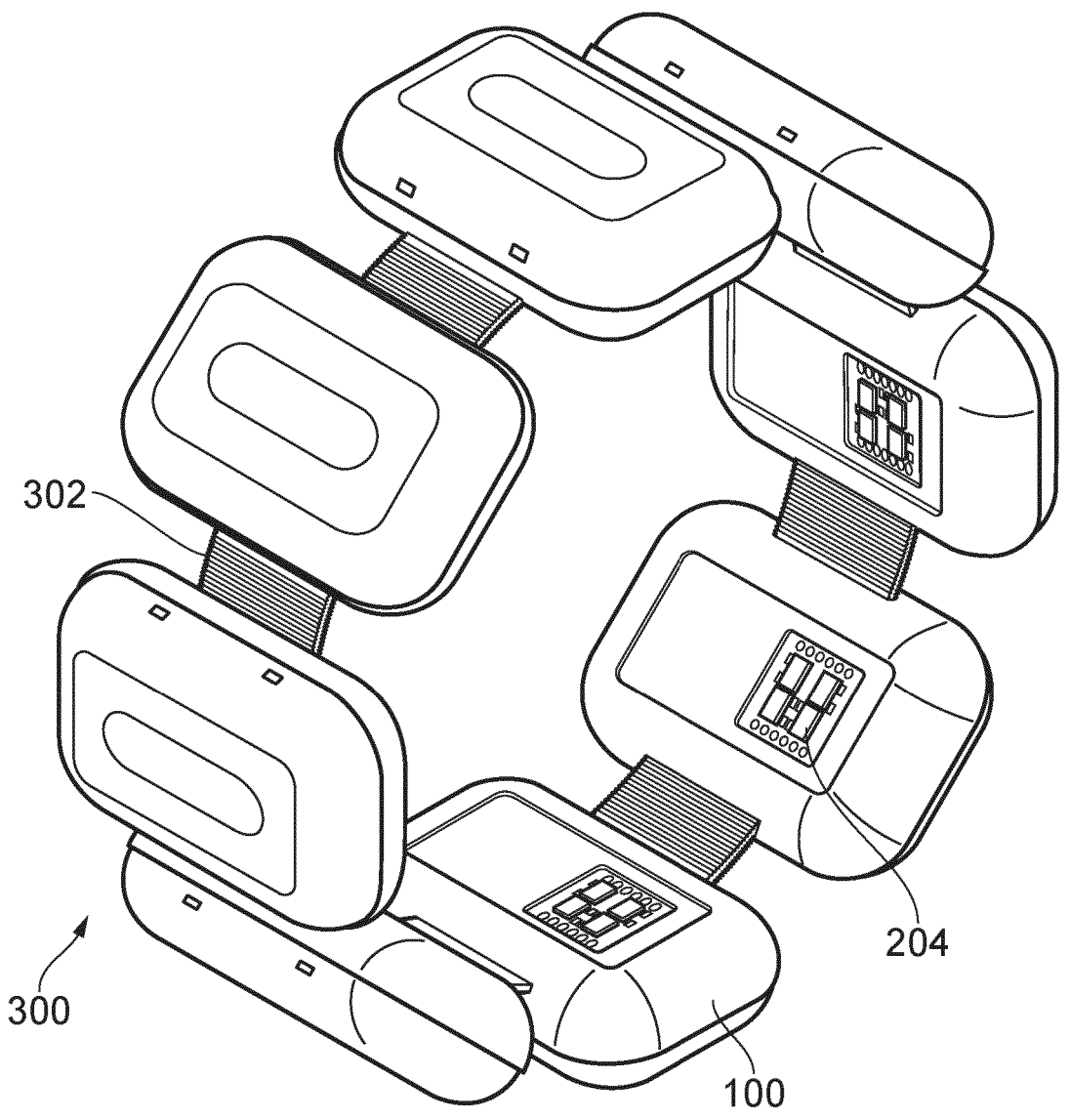
FIG. 3 is a perspective view of a wearable biomagnetic sensing device that is an embodiment of the invention.

FIG. 3 illustrate an example of a wearable biomagnetic sensing device 300 that incorporates a plurality of the biomagnetic sensor modules 100 discussed above. Each module 100 is enclosed in a respective protective shell that has a biocompatible undersurface through which the sensor unit 204 is capable of detecting biomagnetic signals. In this example eight modules 100 are interlinked in a ring by an elastic strap 302. This configuration may be suitable for wearing on a user's wrist. The elastic strap 302 permits the device 300 to easily mounted, e.g. by slipping it up or down the wrist, whilst also ensuring that data can be gathering with minimal motion artifacts by ensuring the device is retained in place in use. In other examples, the device 300 may be used in conjunction with motion sensors which allow the measured biomagnetic data to be combined with motion information.

Figure 4:
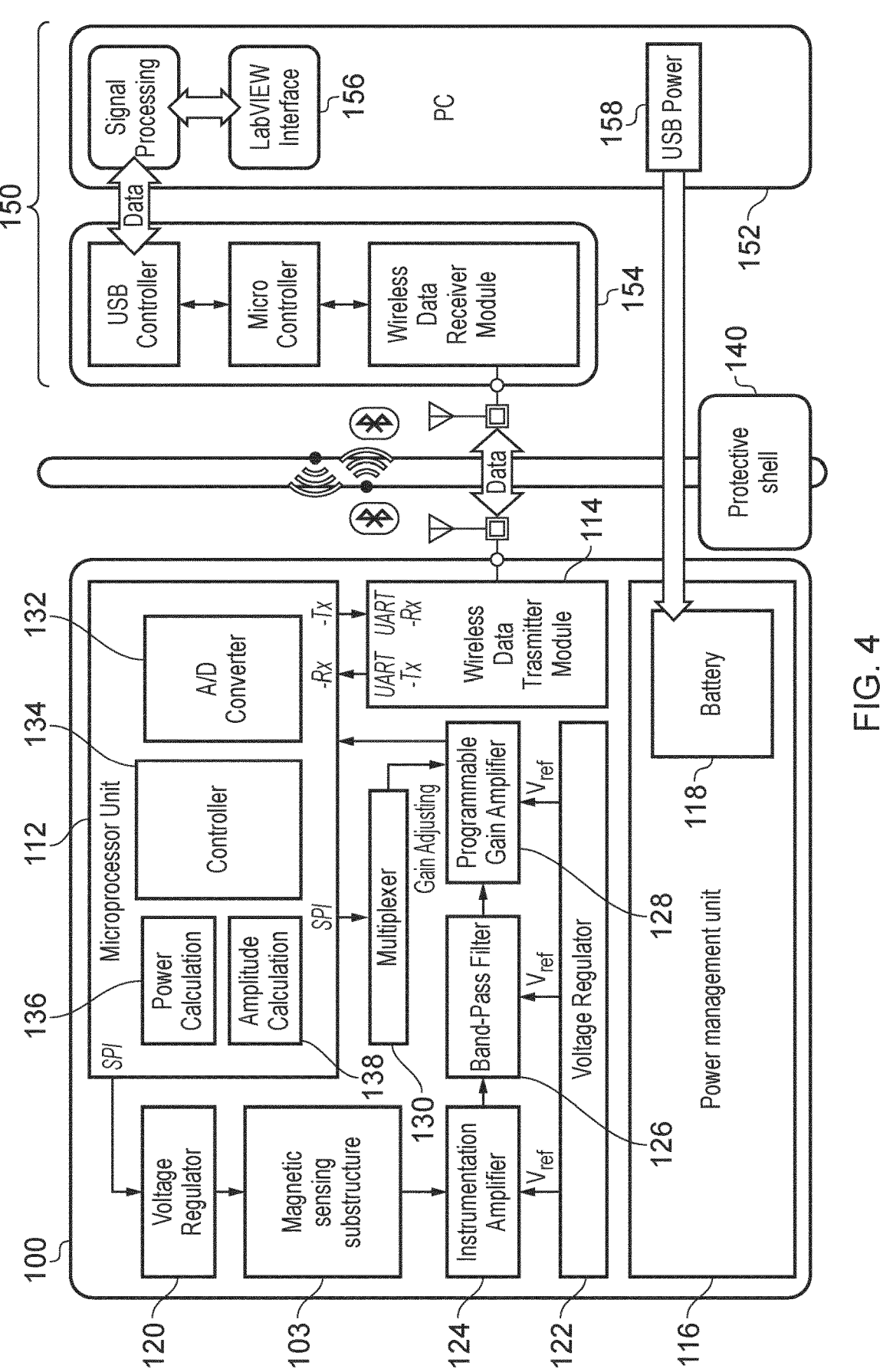
FIG. 4 is a schematic diagram illustrating a processing flow between functional components of the biomagnetic sensor module of FIG. 1.

FIG. 4 is a schematic diagram illustrating a processing flow between functional components of the biomagnetic sensor module 100 discussed above, and communications between the module 100 and an external computing system 150. In this example, the control circuitry 112 of the module 100 comprises a microprocessor unit that interacts with the magnetic sensing substructure 103 and analogue read out circuitry via respective voltage regulators 120, 122 under the control of power and amplitude calculation modules 136, 138, which ensure that they receive a stable power supply. As discussed above, the magnetic sensing substructure 103 includes the primary sensing layer that provides signals from one or more sensor units, each of which have four TMR sensors in a Wheatstone bridge arrangement. The control circuitry permits real-time readout of signals from the sensor units. The Wheatstone bridge preferably operates in the voltage mode, but it may also be possible to configure the module to be selectively operable in either the voltage-mode or the current-mode, e.g. by using a selector actuator such as a toggle switch. The sensitivity in the current-mode with for a given change in resistance is twice larger than the voltage-mode. It is also highly desirable for the sensor output to exhibit stability and over a range of temperatures commensurate with expected use conditions (e.g. $-20°$ C. to $50°$ C.). Integrating the TMR sensors in full Wheatstone bridges provides a null-voltage output in the absence of an external stimulation field, while ensuring that each device within the arrangement outputs a full signal that can be utilized in a differential amplifier.

As mentioned above, the magnetic sensing substructure 103 includes gradiometer that measures dynamic magnetic background noise that can be subtracted from the signal measured by the primary sensing layer. Conventionally, to reduce noise sources such as the acoustic noise and disturbances of magnetic and electric fields from the earth and surrounding equipment, it has been necessary to operate a magnetic sensing system in a magnetically shielded environment. In the present invention, the use of a gradiometer to compensate for dynamic magnetic background noise provides the device with a sensitivity comparable to previous designs (~20 pT) but a higher dynamic range (target~50 pT) without magnetically shielding.

Figure 5:
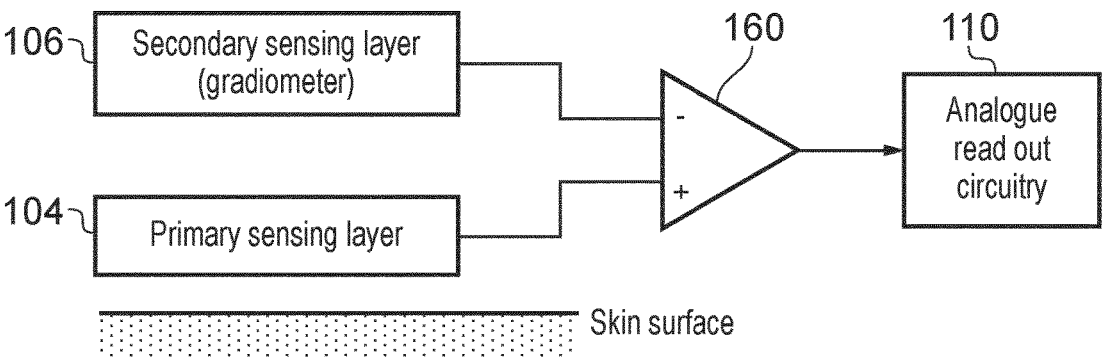
FIG. 5 is a schematic diagram illustrating the configuration of a gradiometer in the biomagnetic sensor module of FIG. 1.

FIG. 5 is a schematic diagram illustrating the configuration of the gradiometer in the active noise cancellation unit 111. The secondary sensing layer 106 comprises a plurality of TMR sensor units of the same type as those in the primary sensing layer. However, instead of being configured to detect a magnetic field at the skin surface, the TMR sensor units in the secondary sensing layer 106 are configured as one or more gradiometers to record dynamic magnetic background noise. In a preferred example, three gradiometers are provided in a triaxial arrangement, with a plurality of TMR sensors being integrated into a miniaturised Wheatstone bridge configuration for each axis of the gradiometer. The signals from these gradiometers are combined at a pick-up sensor to provide a background signal that is independent of the orientation of the device. The background signal is provided to an inverting input of a comparator 160 (differential amplifier), at which it is subtracted from a signal provided from the primary sensing layer 104. The output of the comparator 160 is sent to the analogue read out circuitry 110. Real time compensation for dynamic magnetic background noise therefore occurs at the front end of the module 100. This dramatically improves the system's tolerance of large DC earth fields and AC environmental noise.

Figure 6:
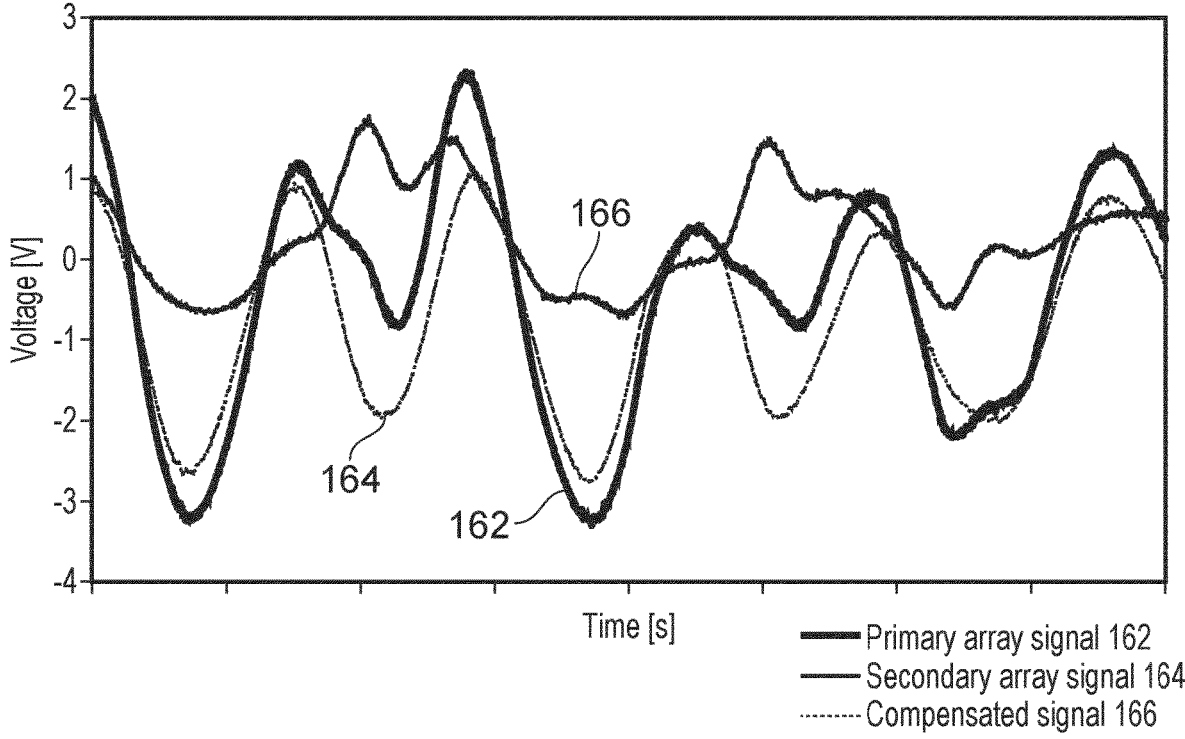
FIG. 6 is a graph showing the effect of a gradiometer compensation technique.

FIG. 6 shows a graph showing the experimental results of using a triaxial gradiometer in the manner outlined above. The proposed active noise cancelling is based on the principle of phase cancellation, where background magnetic noise 164 is recorded, inverted to create "anti-noise," and then added the output signal 162 of the primary sensing layer, which includes the desired biomagnetic signals. The anti-noise signal cancels out the actual background magnetic noise to provide a compensated signal 166 that is output to the analogue read out circuitry.

It is desirable to sample the ambient magnetic noise and line up its phase with the measured signal as accurately as possible to provide the maximum degree of attenuation. Whilst 100% noise cancellation is not feasible in a practical system, the gradiometer compensation technique disclosed herein can achieve noise reduction of 20-40 dB, which cuts the background noise level to between one-quarter to one-sixteenth its original level.

Returning to FIG. 4, the output from the magnetic sensing substructure 103 is receive by the analogue read out circuitry 110, which in this example includes a transimpedance amplifier (not shown), an instrumentation amplifier 124, bandpass filter 126, a programmable gain amplifier 128, and an analogue multiplexer 130, which selectively connects a signal from each channel in the magnetic sensing substructure 103 to an analogue-to-digital converter (ADC) 132, which may be part of the microprocessor unit. The transimpedance amplifier is utilized to sense the current signals generated from the TMR sensors and convert them into voltage readout with a maximum signal-to-noise ratio for subsequent signal processing. The bandpass filter 126 may be a high-order filter that adopts a Sallen-key topology with a cut-off frequency from 300 to 500 Hz. In other examples, the bandpass filter 126 may comprise a 20th-order Butterworth filter have a bandpass region of 30 to 300 Hz. The filtered signal is converted into digital data through the ADC 132, which in this example is an 18-bit successive approximation register ADC that offers high speed, high accuracy, low-power and low-cost.

The converted digital signals can be transmitted through wireless communications module 114 to the external computing system 150. In this example, the external computing system 150 may comprise a computer (e.g. laptop or desktop device) 152 and a smartphone 154, which permits data to be displayed rapidly in a convenient manner. Data may be communicated between the module 100 and smartphone 154 through the protective shell 140 of the module a conventional wireless communications protocol, e.g. Bluetooth® or the like. The protective shell 140 may be configured to as a magnetic shield to reduce external magnetic noise in the module 100. The smartphone 154 may be connectable to communicate with the computer 152, e.g. via a USB interface or wireless connection, whereby the digital signals can be extracted, classified, and displayed in a LabVIEW interface 156 on the computer.

Figure 7:
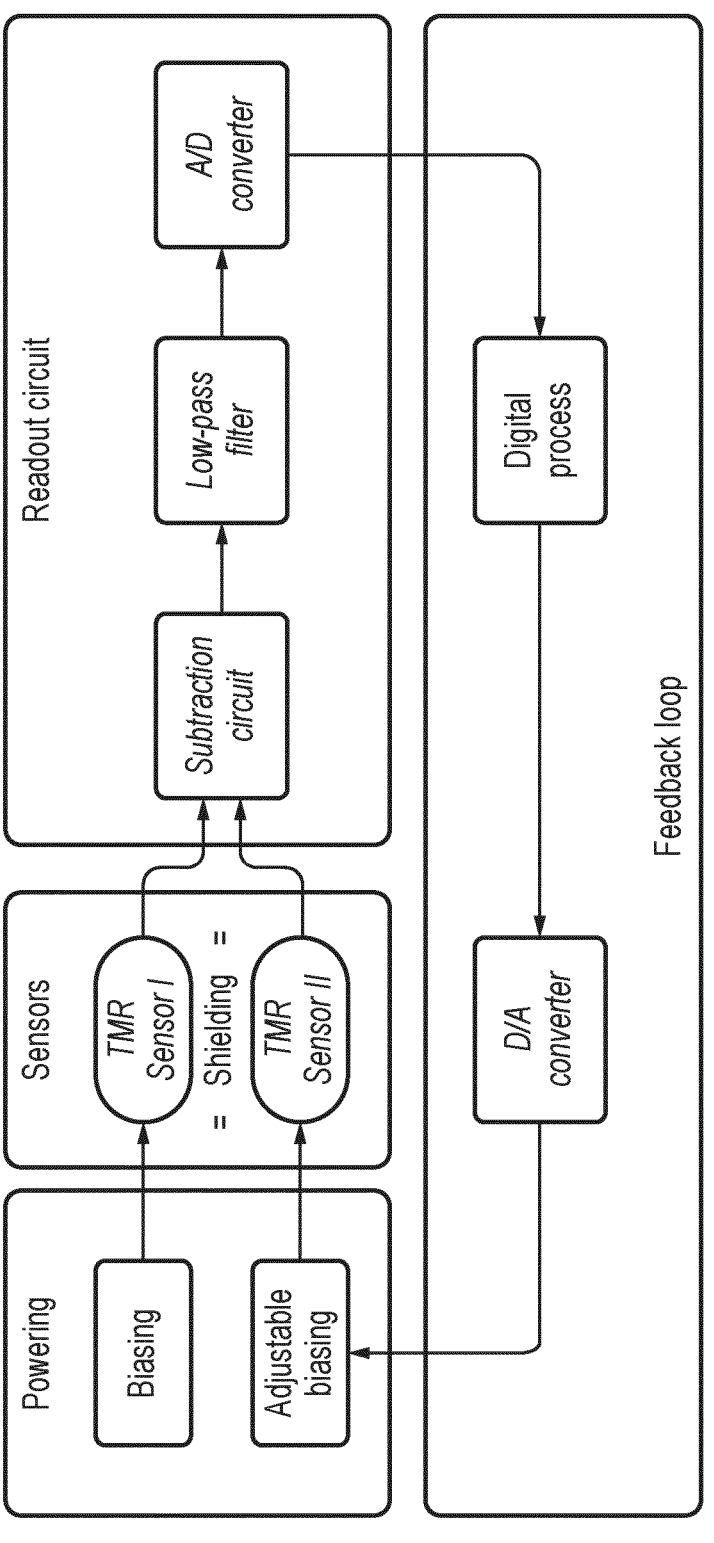
FIG. 7 is a schematic diagram illustrating a baseline compensation technique that can be used in the biomagnetic sensor module of FIG. 1.

FIG. 7 is a schematic diagram illustrating a baseline compensation arrangement that can be used in the biomagnetic sensor module discussed above. The baseline compensation arrangement is used to compensate for the intrinsic mismatch between the TMR sensor unit(s) in the primary sensing layer 104 and the secondary sensing layer 108 and the mismatch introduced by the shielding layer 106. This compensation can be achieved either by controlling the bias of the reference TMR sensor units in the secondary sensing layer 108 (i.e. the gradiometer unit) through an adjustable current source or by using a variable gain low-noise amplifier to modify an output signal from the secondary sensing layer 108 before it is received by the noise cancellation unit (e.g. subtraction circuit such as the comparator 160 discussed above).

The baseline compensation arrangement is initialised by performing a preliminary step of measuring the baseline output voltages from the primary sensing layer 104 and the secondary sensing layer 108 in the absence of a target magnetic field (i.e. with the biomagnetic sensor module located away from a measurement position). This baseline output is due to the intrinsic mismatch between the TMR sensor units in the primary sensing layer 104 and the secondary sensing layer 108 and the mismatch introduced by the shielding layer 106. This mismatch may then be eliminated by adjusting the setup of the secondary sensing layer 108. In examples that use an adjustable current source to provide a bias signal for the secondary sensing layer 108, this can be done by modifying the bias signal received by the TMR sensor units in the secondary sensing layer 108. In this scenario, the secondary sensing layer 108 would then typically receive a different bias signal from the primary sensing layer 104. Alternatively, in examples that use a variable gain amplifier at the output of the secondary sensing layer 108, this can be done by modifying the gain of that amplifier. By using the output voltage from the readout circuit, a feedback loop is established to set a level for the bias signal or gain that minimizes the baseline output voltage difference. Once the optimal bias level or gain is found, it can be applied to the TMR sensor units of the secondary sensing layer 108 or the low-noise amplifier when a target magnetic field is measured. This reduces the mismatch caused by the sensor and magnetic shield, improving the overall sensitivity and accuracy of the gradiometer configuration.

Figure 8:
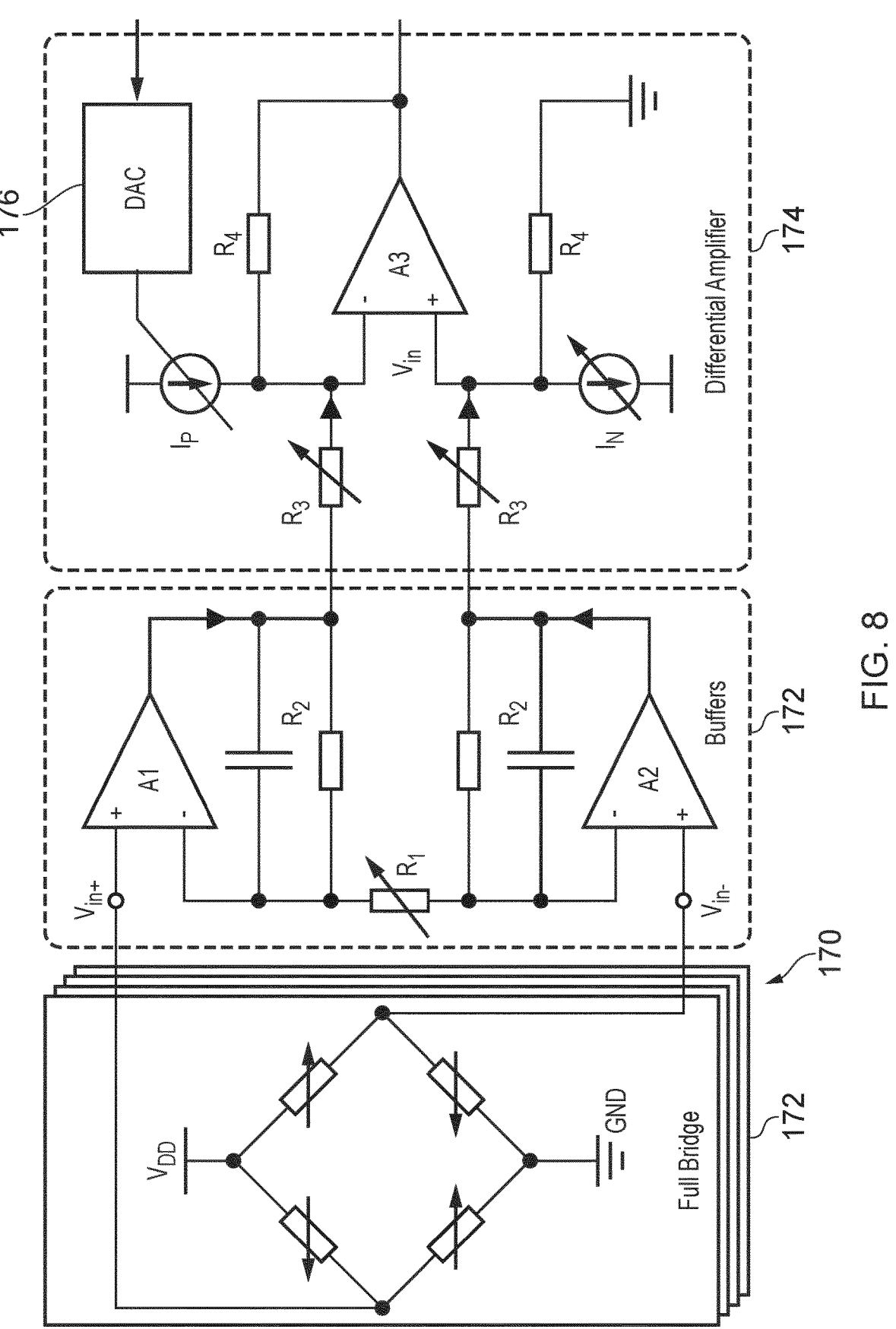
FIG. 8 is a schematic diagram showing a readout circuit architecture that can be used in the biomagnetic sensor module of FIG. 1.

FIG. 8 shows a three-operational amplifier architecture 170 that lies between the Wheatstone bridge arrangements 172 for each channel of the primary sensing layer 104 and secondary sensing layer 106 and the comparator 160. Each Wheatstone bridge arrangement 172 comprises a plurality of TMR sensor arrays arranged to provide differential input signals $V_{in+}$ and $V_{in-}$. The architecture 170 comprises an input buffer stage 172 followed by a differential amplifier stage 174, following which the signals are conveyed to the comparator 160 so that the background noise can be removed from the measurement signal before it is provided to the analogue read out circuitry 110.

The input buffer stage 172 and differential amplifier stage 174 are implemented using a three operational amplifier architecture. Two low noise input amplifiers A1, A2 are used in the input buffer stage 172. A third amplifier A3 is used in the differential amplifier stage 174. As described in more detail below, this architecture can be configured to achieve a high input impedance and excellent linearity, as well as extend the input range by using rail-to-rail input stages.

The control circuitry 112 (e.g. microprocessor unit) is arranged to generate control signals for the architecture 170. One control signal may be used to set the gain of input buffer stage 172 through adjustment of variable resistance $R_1$, which is connected to the control circuitry 112 through a digital-to-analog converter (DAC) 176. Similarly, another control signal may be used to set the gain of differential amplifier stage 174 through adjustment of variable resistance $R_3$. In the latter case, the output offset of the three-operational amplifier is adjustable using a digital-to-analog converter (DAC) connected to the input of the fully differential amplifier A3. The DAC 176 may thus set the currents $I_P$ and $I_N$ to adjust the resistance $R_3$. The control circuitry 112 may also generate a common-mode feedback (CMFB) control signal to set the bias current of the differential amplifier stage 174.

The two input amplifiers A1, A2 may use chopping to eliminate the input offset and low frequency flicker noise by means of chopper switches which enable a modulation-demodulation technique. For example, the two amplifiers A1, A2 in the input buffer stage 172 may have an input chopper switch (not shown) that modulates the differential input signals $V_{in+}$ and $V_{in-}$ up to a chopping frequency, which facilitates elimination of upmodulating offset and low-frequency flicker noise. The amplifier A3 in the differential amplifier stage 174 may have a chopping output stage configured to reintegrate the signal. The chopping output stage may comprise chopper switches arranged to synchronously demodulate the signal back to its original frequency, whilst causing offset and 1/f noise of the amplifier input stage to be modulated to the chopping frequency. The chopper switches driven by respective control signals from the microcontroller, which implements a suitable modulation/demodulation process. The chopping frequency is typically selected to be between a few hundred Hz and several kHz. The chopping frequency is selected to be greater than (at least double) the sampling frequency of the ADC 132 to prevent errors due to aliasing.

A common-mode feedback (CMFB) circuit may be employed to maintain a DC voltage output. The CMFB circuit operates to stabilize the common-mode voltage by adjusting the common-mode output currents. In this example, the CMFB circuit is configured to detect the common-mode voltage by obtaining an average of the differential output voltages from the amplifier A3, compare the obtained average with a reference voltage, and return the difference voltage between the average and the reference to the bias network of the differential amplifier stage 174. There the difference voltage is converted to a common-mode output current to adjust the common-mode voltage. As a result, it cancels the output common-mode current components and fixes the DC outputs to a desired level. Typically the reference voltage may be set to be half the rail voltage.

The transfer function of the proposed three-operational amplifier structure including the DAC operation is expressed as $$V_{out} = \left(1 + \frac{2R_2}{R_1}\right)\left(\frac{R_4}{R_3}\right)(V_{in+} - V_{in-}) + R_4(I_P + I_N)$$

Figure 9A:
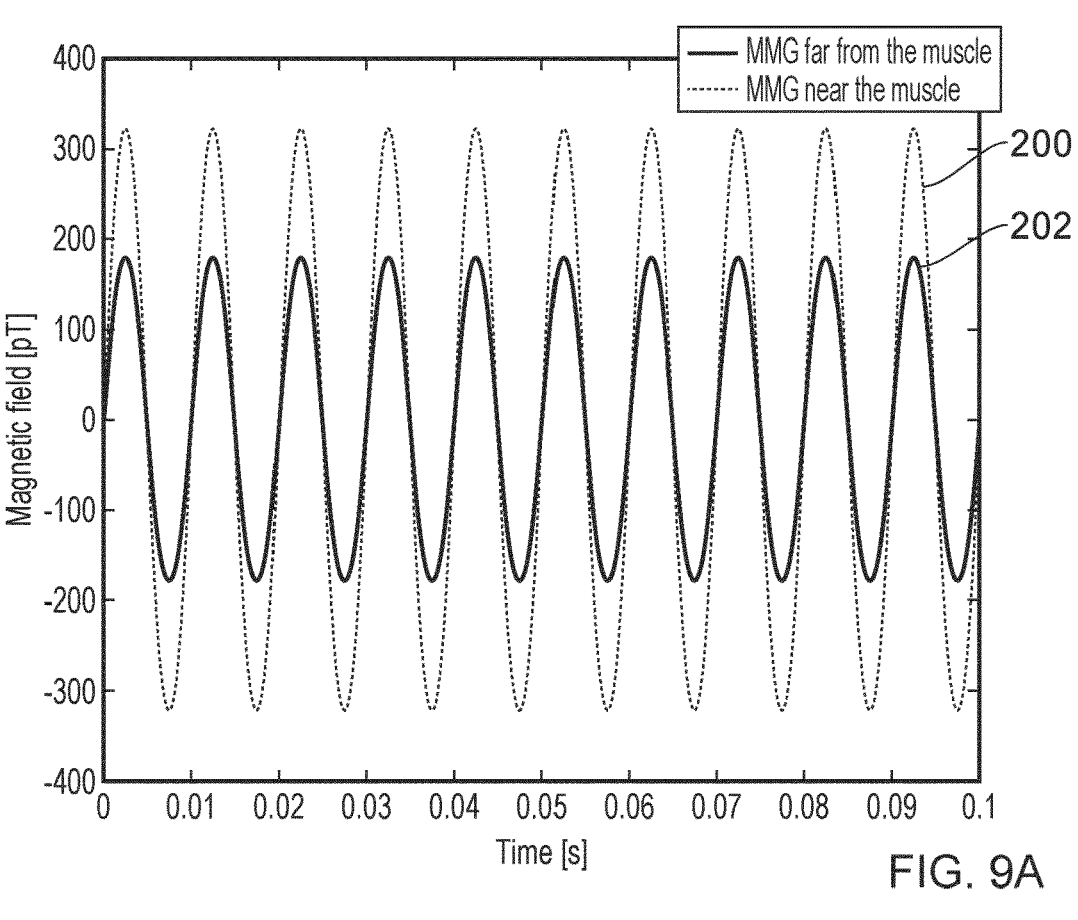
FIGS. 9A and 9B are simulated graphs that illustrate the relative magnitude of MMG and noise magnetic signals that are handled by the biomagnetic sensor module.

FIG. 9A is a graph that shows simulated MMG signals that were used to simulate the effect of the noise cancelling technique discussed above. The graphs shows two simulated MMG signals 200, 202 having different amplitudes. The first signal 200 represents an MMG signal near the muscle from which it originates. The first signal 200 has a frequency of 100 Hz and an amplitude of 322 pT. The second signal 202 represents the same MMG signal 20 mm further from the muscle than the first signal 200. The second signal 202 has a frequency of 100 Hz and an amplitude of 177 pT, to illustrate the manner in which the signal attenuates as the distance from the muscle increases. Providing a shielding layer between the TMR sensors in the primary sensing layer 104 and the secondary sensing layer 108 provides further attenuation with the effect that the MMG signal can be treated as essentially negligible at the TMR sensors in the secondary sensing layer 108.

Figure 9B:
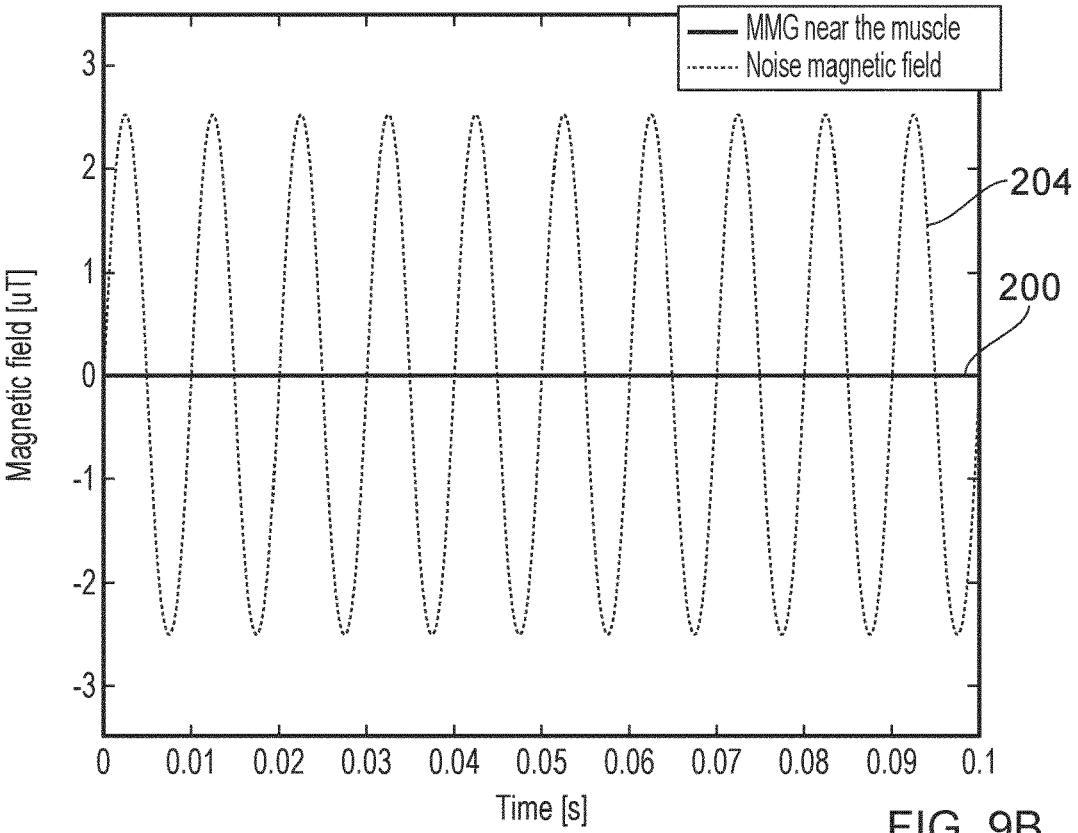

FIG. 9B is a graph that illustrate the relative magnitude of a noise signal 204 experienced by the TMR sensors in the primary sensing layer 104 and the secondary sensing layer 108 compared with the MMG signal 200 near the muscle from which it originates. The noise signal 204 in this example was simulated as a 10 Hz signal with an amplitude of 2.5 pT, which is an order of magnitude higher than the MMG signal 200. As discussed above with reference to FIG. 6, running the simulation to apply an inverse of the simulated noise signal at the TMR sensors in the secondary sensing layer 108 to the simulated noise and MMG signal at the TMR sensors in the primary sensing layer 104 demonstrated that the MMG signal could effectively be extracted despite the relatively high amplitude of the noise signal.

In a further embodiment, the noise cancelling techniques discussed above may be further enhanced by combining the biomagnetic sensor module described herein with existing bioelectric sensors (e.g. ECG sensors or the like). The bioelectric sensors provide a complimentary sensed output from which it is possible to remove noise from spectrally-similar signals using on-chip signal processing of the biomagnetic signals. In practice this is implemented using a reservoir computing (RC) technique in which outputs from both EMG and MMG sensors are analysed to recognise and separate 1/f noise from the MMG signal. The use of a physical reservoir computing implementation is beneficial in offering much low training time and memory requirements because the sensors operate as physical RC model units [13].

Figure 10:
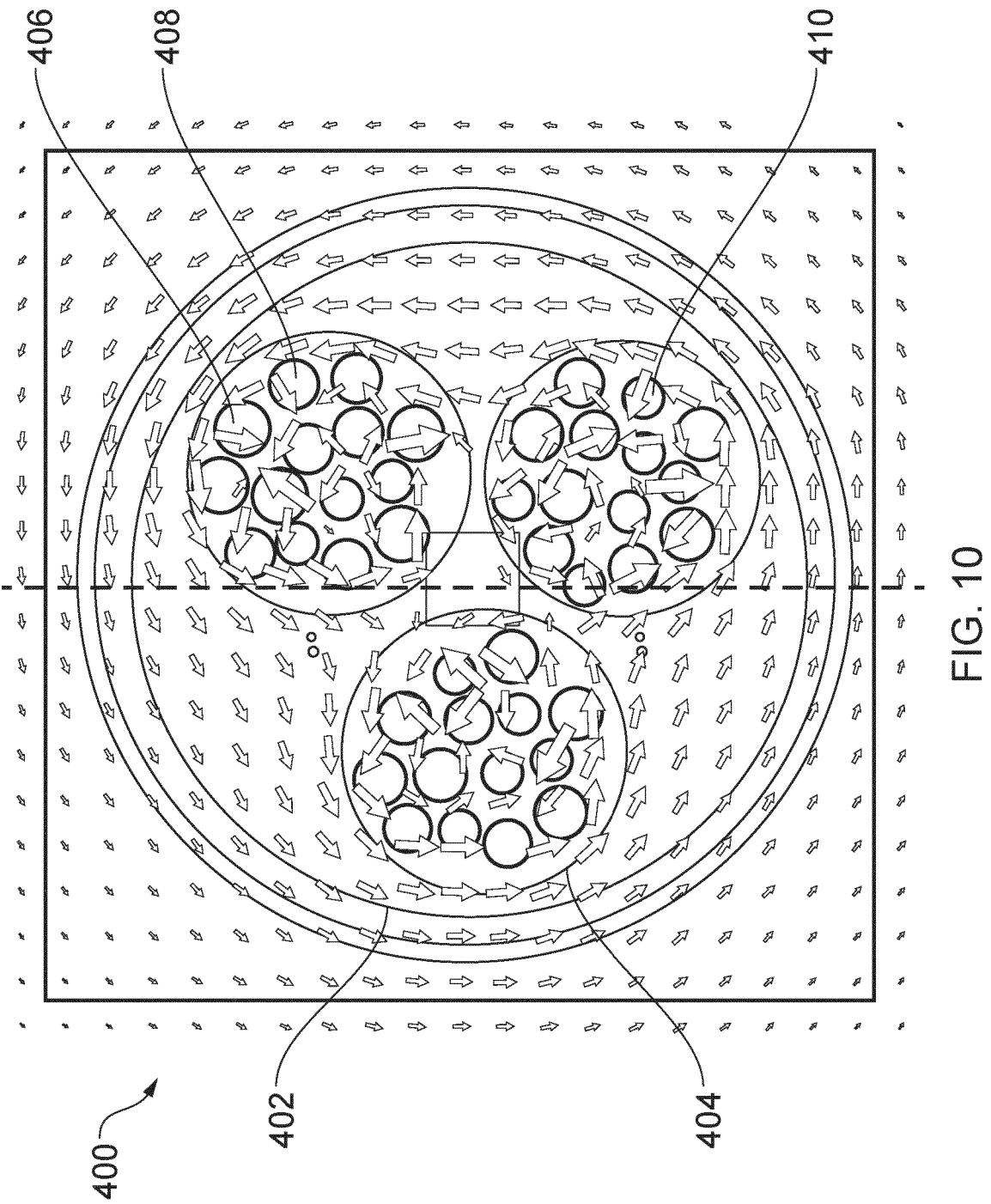
FIG. 10 shows a cross-section through a representation of muscle tissue used in a system for simulating biomagnetic field potential.

To explore the practicality of using the biomagnetic sensor module discussed above, a model was established for simulating biomagnetic field potential. FIG. 10 shows a cross-section through a representation 400 of muscle tissue 402 used in this simulation model. The image in FIG. 10 shows a cross-sectional area of muscle tissue 402 (orthogonal to the fibre direction) consisting of a plurality of fascicles 404 each having multiple fibres 406, 408, 410 belonging to different motor units. Each muscle fibre carries an electrical current (propagating action potential). The model simulates in temporal and spatial domains the combined effect of the magnetic field generated from a time-changing action potential propagating in a group of skeletal muscle cells based on the different currents in each type of muscle fibre.

Figures 11A, 11B:
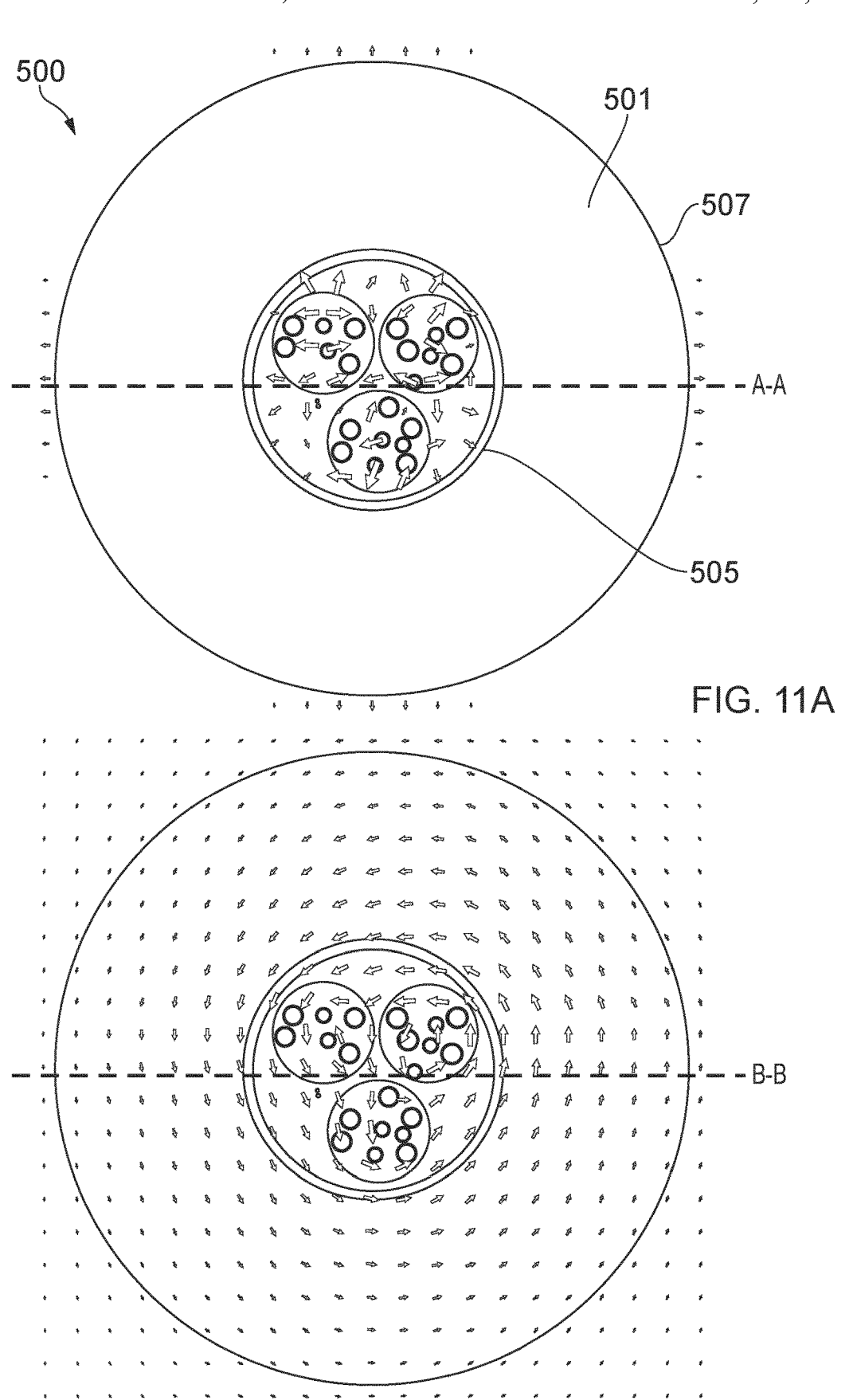
FIG. 11A shows a cross-section through a representation of muscle tissue showing a simulated electric field potential in muscle tissue in the absence of a layer of fat.
FIG. 11B shows a cross-section through the representation of muscle tissue of FIG. 11B showing a simulated magnetic field potential.

The layers between the muscle and skin surface, known as volume conduction, play a critical role during signal measurement. The simulation model discussed above was used to obtain finite-difference time-domain simulations to study the volume conduction effect on the electrical and magnetic signals. FIG. 11A shows a cross-section through a representation 500 of muscle tissue showing a simulated electric field potential in the volume 501 between the muscle fascicle 505 and skin surface 507 in the absence of a layer of fat. FIG. 11B shows the same cross-section but showing a simulated magnetic field potential.

Figures 11C, 11D:
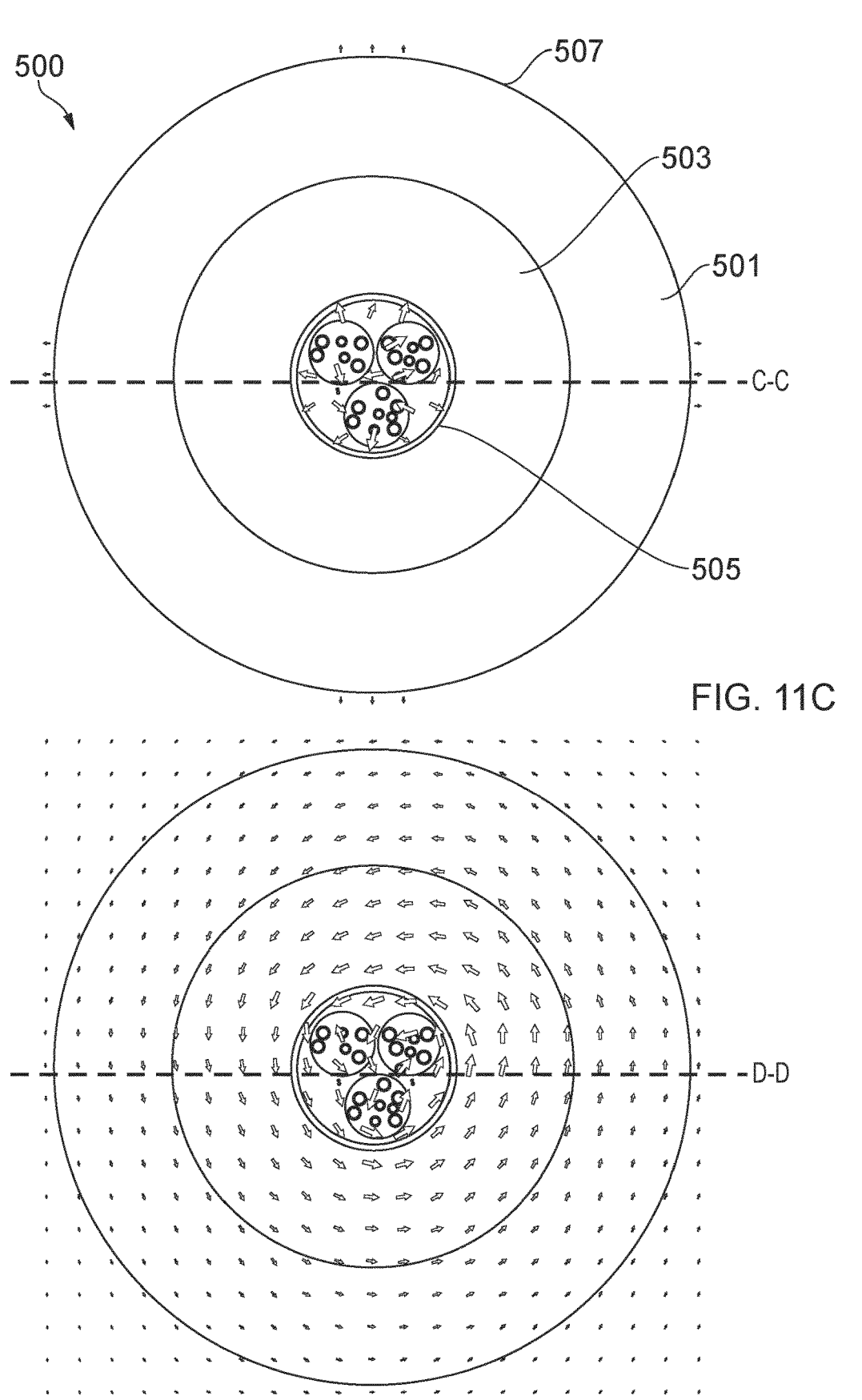
FIG. 11C shows a cross-section through a representation of muscle tissue showing a simulated electric field potential in muscle tissue with a layer of fat around the muscle fascicle.
FIG. 11D shows a cross-section through the representation of muscle and fat tissue of FIG. 11C showing a simulated magnetic field potential.

FIG. 11C shows a cross-section through another representation of muscle tissue showing a simulated electric field potential in in the volume 501 between the muscle fascicle 505 and skin surface 507 with a layer of fat 503 around the muscle fascicle. FIG. 11D shows the same cross-section but showing a simulated magnetic field potential.

Figure 12:
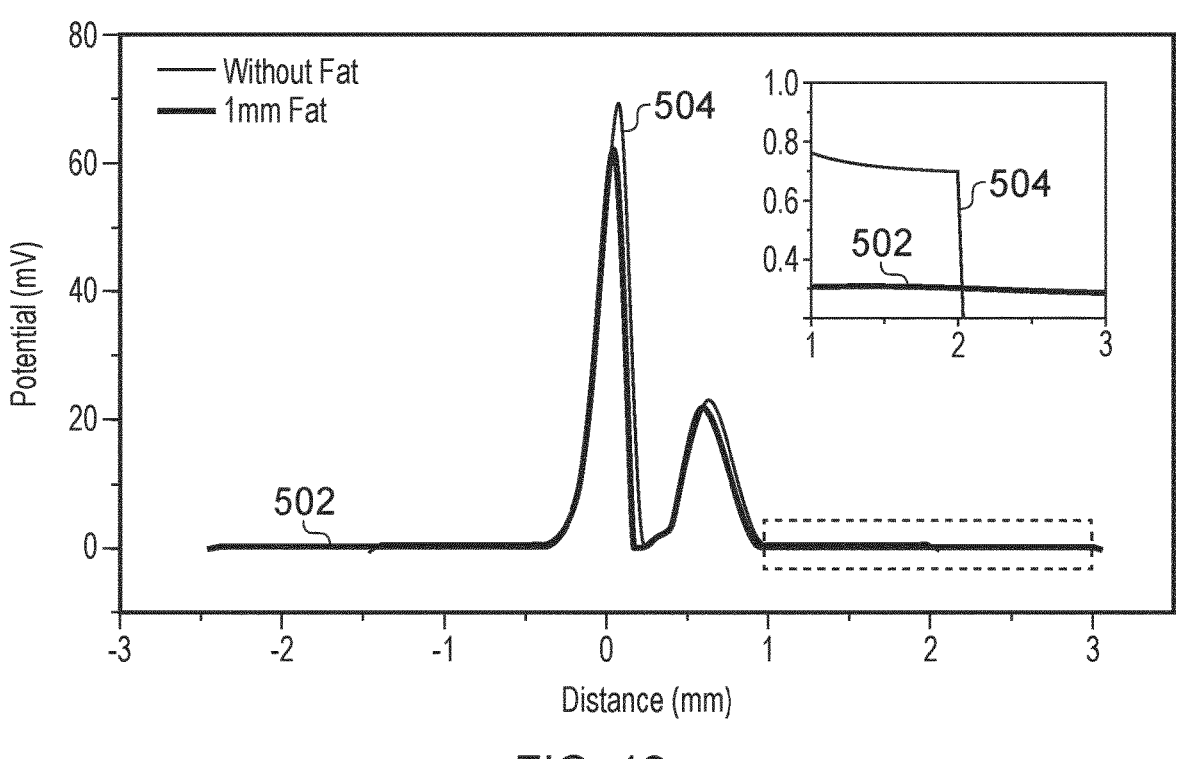
FIG. 12 is a graph showing variations in simulated electric field potential through lines A-A and C-C in FIGS. 11A and 11C.
Figure 13:
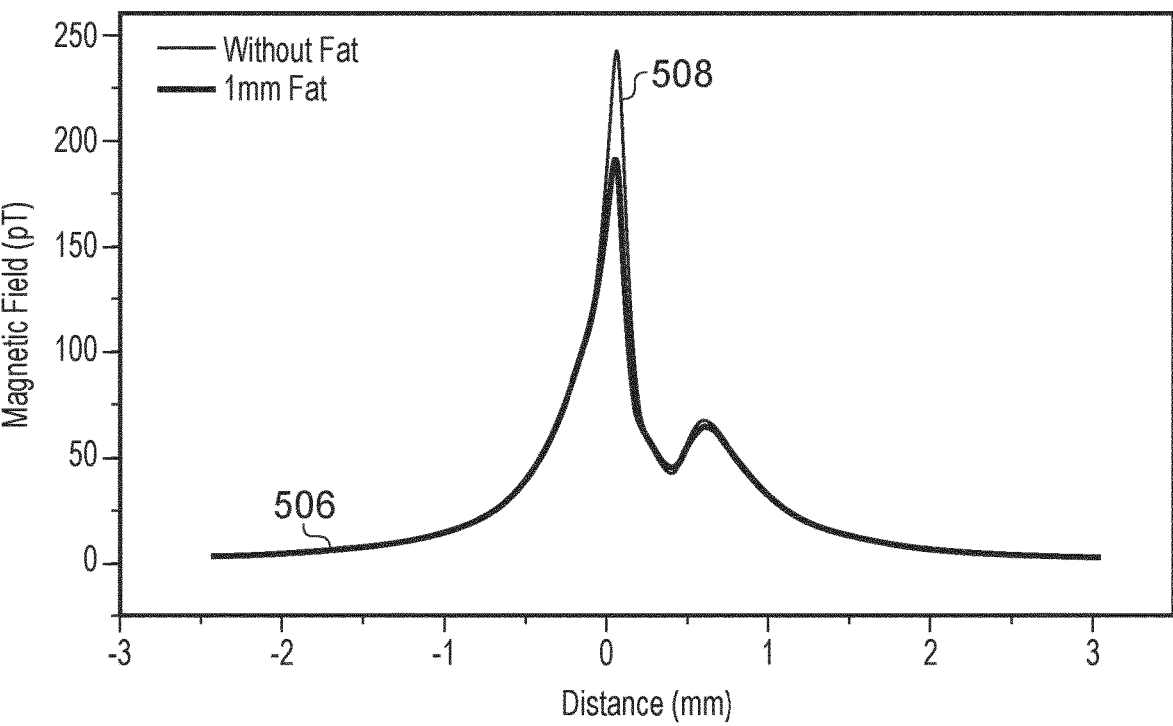
FIG. 13 is a graph showing variations in simulated magnetic field potential through lines B-B and D-D in FIGS. 11B and 11D.

FIG. 12 is a graph showing variations in simulated electric field potential through lines A-A and C-C in FIGS. 11A and 11C. FIG. 13 is a graph showing variations in simulated magnetic field potential through lines B-B and D-D in FIGS. 11B and 11D. It can be seen from the inset of FIG. 12 that the addition of a 1 mm layer of fat causes the electrical signal 502 to decline by 60% compared with the electrical signal 504 at the skin surface, whereas the magnetic field potential did not change. The layers separating the skin and signal source are thus transparent for the magnetic field but act to perturb the electrical field.

Figure 14:
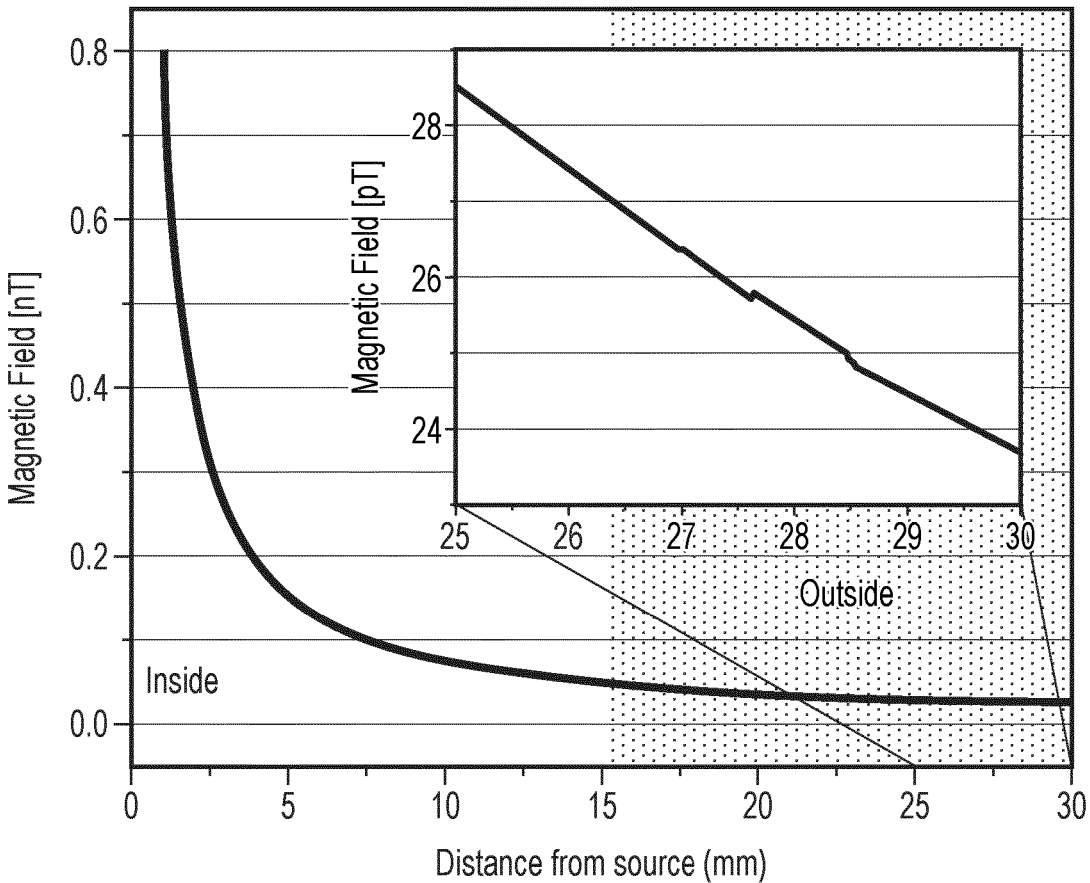
FIG. 14 is a graph showing a simulated illustration of change in biomagnetic potential with distance from its source in muscle tissue.

FIG. 14 is a graph showing a change in biomagnetic potential with distance from its source in muscle tissue. The graph was obtained using the simulation model discussed above. It can be seen that the magnitude of the biomagnetic potential drops rapidly from the source and is already approaching 50 pT at the surface of the skin. However, it can be seen that in a zone of 25-30 mm from the source (10-15 mm from the surface of the skin) the magnitude of the biomagnetic field is in the range 24-28 pT, which falls within the sensitivity range of the TMR sensors discussed above. The magnitude of the field is still falling in this detection zone, so the secondary sensing layer will experience a significantly lower biomagnetic field. Providing a shielding layer between the primary sensing layer and second sensing layer as discussed with respect to FIG. 1 can ensure that the biomagnetic field is negligible at the secondary sensing layer.

As explained above, the biomagnetic sensing device of the invention can use a combination of different techniques for cancelling the noises in the environment (i.e., Earth's magnetic field, thermal and 1/f noise):

1) Readout circuit techniques such as chopping and auto-zeroing to compensate the offset
2) Gradiometer integration on the chip using another TMR sensor to record a geomagnetic field
3) Utilizing thermo-stability material layers at device fabrication level to stabilize the temperature.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about"

one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

REFERENCES

A number of publications are cited above in order to more fully describe and disclose the invention and the state of the art to which the invention pertains. Full citations for these references are provided below.

The entirety of each of these references is incorporated herein.

[1]J. Malmivuo and R. Plonsey, Bioelectromagnetism: principles and applications of bioelectric and biomagnetic fields. Oxford University Press, USA, 1995.

[2]D. B. Geselowitz, 'Magnetocardiography: an overview', IEEE Transactions on Biomedical Engineering, no. 9, pp. 497-504, 1979.

[3]R. Fenici, D. Brisinda, and A. M. Meloni, 'Clinical application of magnetocardiography', Expert Review of Molecular Diagnostics, vol. 5, no. 3, pp. 291-313, 2005.

[4]S. Baillet, 'Magnetoencephalography for brain electrophysiology and imaging', Nature Neuroscience, vol. 20, no. 3, pp. 327-339, 2017.

[5]E. Boto et al., 'Moving magnetoencephalography towards real-world applications with a wearable system', Nature, vol. 555, no. 7698, p. 657, 2018.

[6]S. Zuo, H. Heidari, D. Farina, and K. Nazarpour, 'Miniaturized magnetic sensors for implantable magnetomyography', Advanced Materials Technologies, no. 2000185, 2020.

[7]S. Zuo et al., 'Ultrasensitive Magnetoelectric Sensing System for pico-Tesla MagnetoMyoGraphy', IEEE Transaction on Biomedical Circuits and Systems, 2020.

[8]B.-M. Mackert, 'Magnetoneurography: theory and application to peripheral nerve disorders', Clin. Neurophysiol., vol. 115, no. 12, pp. 2667-2676, 2004.

[9]C.-H. Im, S. C. Jun, and K. Sekihara, 'Recent advances in biomagnetism and its applications'. Springer, 2017.

[10]R. Kleiner, D. Koelle, F. Ludwig, and J. Clarke, 'Superconducting quantum interference devices: State of the art and applications', Proceedings of the IEEE, vol. 92, no. 10, pp. 1534-1548, 2004.

[11]S. Zuo, K. Nazarpour, and H. Heidari, 'Device modelling of MgO-barrier tunnelling magnetoresistors for hybrid spintronic-CMOS', IEEE Electron Device Letter, vol. 39, no. 11, pp. 1784-1787, 2018.

[12]H. Heidari, S. Zuo, A. Krasoulis, and K. Nazarpour, 'CMOS Magnetic Sensors for Wearable Magnetomyography', 2018 40th International Conference of the IEEE Engineering in Medicine and Biology Society (EMBC), Honolulu, HI, 2018, pp. 2116-2119.

[13] Liang, X., Zhong, Y., Tang, J. et al. Rotating neurons for all-analog implementation of cyclic reservoir computing. Nat Commun 13, 1549 (2022).

The invention claimed is:

1. A biomagnetic sensor module comprising:
a tunnelling magnetoresistive (TMR) sensor unit configured to output a detection signal indicative of a magnetic field adjacent to biological tissue;
a gradiometer unit configured to output a background signal indicative of ambient magnetic noise;

a shielding element located between the TMR sensor unit and the gradiometer unit;
an active noise cancellation unit configured to remove the background signal from the detection signal to generate a biomagnetic signal;
analogue read out circuitry configured to receive the biomagnetic signal and perform signal conditioning to generate an analogue output; and
an analog-to-digital converter (ADC) arranged to generate a digital output signal from the analogue output.

2. The biomagnetic sensor module of claim 1, wherein the gradiometer unit comprises a triaxial gradiometer.

3. The biomagnetic sensor module of claim 1, wherein the gradiometer unit comprises a plurality of TMR sensors configured to detect ambient magnetic noise.

4. The biomagnetic sensor module of claim 1, wherein the TMR sensor unit comprises four TMR sensors in a Wheatstone bridge arrangement.

5. The biomagnetic sensor module of claim 1, wherein the TMR sensor unit is one of a plurality of similarly configured TMR sensor units, wherein each TMR sensor unit is arranged to detect a magnetic field adjacent to biological tissue and output a biomagnetic signal on a respective channel, and wherein the biomagnetic sensor module further comprise a multiplexer configured to selectively couple each respective channel to the analogue read out circuitry.

6. The biomagnetic sensor module of claim 1 further comprises a skin contact interface made from biocompatible material.

7. The biomagnetic sensor module of claim 6, wherein the gradiometer unit is located further from the skin contact interface than the TMR sensor unit.

8. The biomagnetic sensor module of claim 1, wherein the shielding element comprises a magnetically permeable material.

9. The biomagnetic sensor module of claim 1 further comprising a compensation unit configured to minimize a baseline mismatch between the TMR sensor unit and gradiometer unit.

10. The biomagnetic sensor module of claim 9, wherein the compensation unit comprises a feedback circuit configured to receive a baseline output from the TMR sensor and gradiometer unit and adjust the gradiometer unit to minimize the baseline output.

11. The biomagnetic sensor module of claim 9, wherein the compensation unit comprises an adjustable current source configured to generate a bias signal for the gradiometer unit, wherein the bias signal is adjustable to minimize the baseline output.

12. The biomagnetic sensor module of claim 9, wherein the compensation unit comprises a variable gain amplifier connected between the gradiometer unit and the active noise cancellation unit, wherein the gain of the variable gain amplifier is adjustable to minimize the baseline output.

13. The biomagnetic sensor module of claim 1, wherein the TMR sensor unit is arranged in a primary sensing layer and the gradiometer unit is arranged in a secondary sensing layer that lies parallel to and spaced from the primary sensing layer.

14. The biomagnetic sensor module of claim 13, wherein the primary sensing layer is spaced from the secondary sensing layer by a distance equal to or less than 10 mm.

15. The biomagnetic sensor module of claim 13, wherein the active noise cancellation unit and analogue read out circuitry are arranged in one or more layers that lies parallel to and spaced from the secondary sensing layer.

16. The biomagnetic sensor module of claim 1, wherein the analogue read out circuitry comprises a bandpass filter and a common mode feedback circuit.

17. The biomagnetic sensor module of claim 1 further comprises a wireless communication unit configured to transmit the digital output signal to a remote device.

18. A wearable biomagnetic sensing device comprising the biomagnetic sensor module of claim 1.

19. A wearable biomagnetic sensing device of claim 18 comprising a plurality of the biomagnetic sensor modules of claim 1 secured to a retaining element that is mountable on a human body.

20. The wearable biomagnetic sensing device of claim 19, wherein the retaining element is an elastic strap.

* * * * *